United States Patent
Berckmans et al.

(10) Patent No.: US 10,299,715 B2
(45) Date of Patent: May 28, 2019

(54) STRESS MONITORING FOR INDIVIDUALS IN MOVING STRUCTURES

(71) Applicant: BioRICS N.V., Heverlee (BE)

(72) Inventors: Daniel Berckmans, Kessel-Lo (BE); Vasileios Exadaktylos, Thessaloniki (GR)

(73) Assignee: BIORICS N.V., Heverlee (BE)

( * ) Notice: Subject to any disclaimer, the term of this patent is extended or adjusted under 35 U.S.C. 154(b) by 28 days.

(21) Appl. No.: 15/320,532

(22) PCT Filed: Jun. 22, 2015

(86) PCT No.: PCT/EP2015/064012
§ 371 (c)(1),
(2) Date: Dec. 20, 2016

(87) PCT Pub. No.: WO2015/193514
PCT Pub. Date: Dec. 23, 2015

(65) Prior Publication Data
US 2017/0156656 A1    Jun. 8, 2017

(30) Foreign Application Priority Data

Jun. 20, 2014    (GB) .................................. 1411072.0

(51) Int. Cl.
A61B 5/16    (2006.01)
A61B 5/18    (2006.01)
(Continued)

(52) U.S. Cl.
CPC .............. *A61B 5/165* (2013.01); *A61B 5/024* (2013.01); *A61B 5/0205* (2013.01); *A61B 5/11* (2013.01);
(Continued)

(58) Field of Classification Search
None
See application file for complete search history.

(56) References Cited

U.S. PATENT DOCUMENTS 8,284,041 B2 *  10/2012  Cuddihy ................ B60N 2/002
                                                         340/457
2008/0146890 A1    6/2008  Leboeuf
(Continued)

FOREIGN PATENT DOCUMENTS

EP    1392109 B1    8/2005
EP    2711227 A1    3/2014
(Continued)

OTHER PUBLICATIONS

Patterson S M et al., "Automated Physical Activity Monitoring: Validation and Comparison With Physiological and Self-Report Measures", Psychophysiology, pp. 296-305, vol. 30, No. 3 (May 1993).

(Continued)

*Primary Examiner* — Brian T Gedeon
(74) *Attorney, Agent, or Firm* — Browdy and Neimark, PLLC

(57) ABSTRACT

Method and device for monitoring stress of an individual in a moving structure by estimating and monitoring a mental component of a total heart rate of the individual, wherein the total heart rate comprises the mental component, a mechanical component, a component relating to heat balance and a component relating to basic metabolic functions, wherein the total heart rate and movements of the individual and the moving structure are measured in real-time, wherein the mechanical component is estimated in real-time based on the real-time movement of the individual and the moving structure, wherein the mental component is obtained by subtracting the mechanical component, the component relating to the heat balance and the component relating to basic metabolic functions from the total heart rate.

12 Claims, 3 Drawing Sheets

(51) Int. Cl.
*A61B 5/00* (2006.01)
*A61B 5/0205* (2006.01)
*A61B 5/11* (2006.01)
*G16H 50/30* (2018.01)
*A61B 5/024* (2006.01)
*G06F 19/00* (2018.01)

(52) U.S. Cl.
CPC .............. *A61B 5/18* (2013.01); *A61B 5/4866* (2013.01); *A61B 5/7278* (2013.01); *G06F 19/00* (2013.01); *G16H 50/30* (2018.01); *A61B 2562/0219* (2013.01)

(56) References Cited

U.S. PATENT DOCUMENTS

| | | | | |
|---|---|---|---|---|
| 2009/0209829 | A1* | 8/2009 | Yanagidaira | A61B 5/165 600/301 |
| 2009/0312998 | A1* | 12/2009 | Berckmans | A61B 5/024 703/11 |
| 2010/0222687 | A1* | 9/2010 | Thijs | A61B 5/02438 600/508 |
| 2012/0016247 | A1 | 1/2012 | Vrazic | |
| 2014/0067801 | A1 | 3/2014 | Marvit et al. | |
| 2014/0276090 | A1* | 9/2014 | Breed | A61B 5/18 600/473 |

FOREIGN PATENT DOCUMENTS

| | | |
|---|---|---|
| FR | 2998159 A1 | 5/2014 |
| WO | 2008003148 A1 | 1/2008 |

OTHER PUBLICATIONS

Wilhelm F H et al., "Emotions beyond the laboratory: Theoretical fundaments, study design, and analytic strategies for advanced ambulatory assessment", Biological Psychology, pp. 552-569, vol. 84. No. 3 (Jul. 2010).

Taylor C.J. et al., "Environmental time series analysis and forecasting with the Captain toolbox", Environmental Modelling & Software 22:797-814 (2007).

Young P.C., "Recursive estimation and time-series analysis: an introduction for the student and the practitioner. Springer", Heidelberg (2011).

* cited by examiner

STRESS MONITORING FOR INDIVIDUALS IN MOVING STRUCTURES

The present invention concerns a method and a device for monitoring and controlling stress of an individual in a moving structure by estimating and monitoring a mental component of a total heart rate of the individual, wherein the individual may consist of an individual human or an animal.

As explained in international patent application WO2008/003148A1 individuals are living organisms, which are complex, individual, time varying and dynamic (CITD) systems such that monitoring and controlling these systems require complex models. However, as also described in WO2008/003148A1, the European patent EP1392109B1 describes a dynamic and adaptive data-based on-line modelling technique, which manages to model accurately the above CITD systems using only a limited number of parameters. The modelling technique as such is well known in the art (Taylor et al., 2007; Young, 2011).

International patent application WO2008/003148A1 shows that it is possible to calculate mental stress from measurements of total heart rate and activity. The technology allows realising real-time estimates of stress levels of individual humans or animals. Opposite to classical measurement of physiological stress based upon the measurement of EEG, skin conductivity, blood and/or saliva analysis the method allows to measure stress for individuals in full activity since the subject does not need to stay immobile like for e.g. accurate EEG measurements.

From real-time analysis of the dynamic response of heart rate to a variation in the measured body activity it is possible to decompose the total heart rate signal in an activity component and a mental component. The total heart rate can be measured by e.g. a heart rate belt, intelligent textile or a watch. The body activity can be measured by using e.g. a 3D accelerometer and/or an accurate GPS measurement and/or image analysis for example.

The measured total heart rate contains information on different components in body and mind as shown in the following equation (1):

$$HR_{Total} = HR_{Basic\ Met} + HR_{Heat\ Bal} + HR_{Mechanical} + HR_{Mental} \quad (1)$$

wherein $HR_{Total}$ is the measured heart rate;

$HR_{Basic\ Met}$ is the component in the total Heart Rate needed to maintain the Basic Metabolism of the individual; the value of this component depends on e.g. body weight, health status and physical condition, and can be measured e.g. while the individual is lying in the bed in the morning with an empty stomach;

$HR_{Heat\ Bal}$ is the component of the total heart rate that is needed to maintain the heat balance of the body of the individual with a main function to maintain a constant body temperature in different environmental conditions;

$HR_{Mechanical}$ is the mechanical component of the total heart rate due to the mechanical energy the individual is performing during activity such as e.g. walking, running, moving, carrying a load; it may also be referred to as the activity component; $HR_{Mechanical}$ is the movement of the body that requires metabolic energy and consequently heart performance;

$HR_{Mental}$ is the mental component within the total measured heart rate that is due to the mental status or the physiological expression of arousal of the individual.

The equation (1) states that the total measured heart rate contains different components due to different processes going on in body and mind of the individual. This has the consequence that the measured total heart rate will vary when one of these components is varying. When measuring only the total heart rate, it is not known why variations in total heart rate occur and this does not give any insight into the status of body and mind of the individual.

International patent application WO2008/003148A1 describes the methodology to find the value of the mental component, $HR_{Mental}$, out of the total heart rate, $HR_{Total}$. In the method the components $HR_{Basic\ Met}$ and $HR_{Heat\ Bal}$ are considered to be constant for the individual during e.g. training while a sensor is measuring body activity that requires metabolic energy. The dynamic behaviour of the activity signal is analysed in relation with the measured dynamic response of the total heart rate, $HR_{Total}$. From this analysis the value of $HR_{Mechanical}$ can be estimated.

The mental component of the heart rate, $HR_{Mental}$, may be obtained from the above equation (1) when $HR_{Basic\ Met}$ and $HR_{Heat\ Bal}$ are considered to be constant, when $HR_{Mechanical}$ has been estimated from the dynamic relationship with body activity and when $HR_{Total}$ is measured by a heart rate sensor. As such, from the above equation (1) $HR_{Mental}$ is solved as the unknown term.

Hence, according to the present invention, the total heart rate, $HR_{Total}$, comprises a mechanical component, $HR_{Mechanical}$, and the mental component, $HR_{Mental}$. The mechanical component may also be referred to as activity component. The total heart rate, $HR_{Total}$, further comprises a component relating to the heat balance, i.e. $HR_{Heat\ Bal}$, and a component relating to basic metabolic functions, i.e. $HR_{Basic\ Met}$. Furthermore, movement of the individual is measured in real-time and the total heart rate, $HR_{Total}$, is measured in real-time such that the mental component, $HR_{Mental}$, is obtained by subtracting the mechanical component, $HR_{Mechanical}$, the component relating to the heat balance, $HR_{Heat\ Bal}$, and the component relating to basic metabolic functions, $HR_{Basic\ Met}$, from the total heart rate, $HR_{Total}$. Herein, the mental component of the heart rate, $HR_{Mental}$, is a measure for the stress of an individual.

Consequently, a real-time estimation of the stress component, corresponding to the mental component, $HR_{Mental}$, in the heart rate signal is available.

A problem arises when the body of the individual is on and/or in a moving structure such as e.g. bicycle, car, bus, train, ship, airplane and/or trailer. In such case the body movement does not correspond to a heart rate input that is required to realise the accelerations, decelerations or activity of the body. The body movement does not correspond to the body activity that requires metabolic energy or heart rate performance. In those cases the method as described in WO2008/003148A1 does not generate correct data, such that the mechanical component of the heart rate, $HR_{Mechanical}$, may not be estimated based on the movement of the individual.

The objective of the present invention is to realize real-time measurement of stress in individuals when heart rate and body activity of the individual does not correspond to body movement in and/or on moving structures, e.g. during driving a moving structure like a car or motorbike, controlling a moving structure like for example an air plane, a train or when travelling as passenger in such moving structures like for example an air plane, a ship, a train, a horse trailer, etc.

The above mentioned objective is realised by the method and device having the specific features set out in the appended claims. Specific features for preferred embodiments of the invention are set out in the dependent claims.

Practically, in the method and device, according to the invention, besides the movement of the individual, movement of the moving structure is measured in real-time and the mechanical component of the heart rate, $HR_{Mechanical}$, is estimated in real-time based on the real-time movement of the individual and the real-time movement of the moving structure. A dynamic and adaptive data-based on-line modelling technique can be used for this purpose.

Herein, relative movement of the individual in relation to the moving structure is, preferably, calculated and/or estimated based on the real-time movement of the individual and the real-time movement of the moving structure. Furthermore, the mechanical component of the heart rate, $HR_{Mechanical}$, is, preferably, estimated in real-time based on the relative movement of the individual in relation to the moving structure.

Other particularities and advantages of the invention will become clear from the following description and accompanying drawings of a practical embodiment of the method and device of the invention; the description and drawings are given as an example only and do not limit the scope of the claimed protection in any way.

FIG. 3 shows stress levels as function of distance and on the race track.

Figure 4:
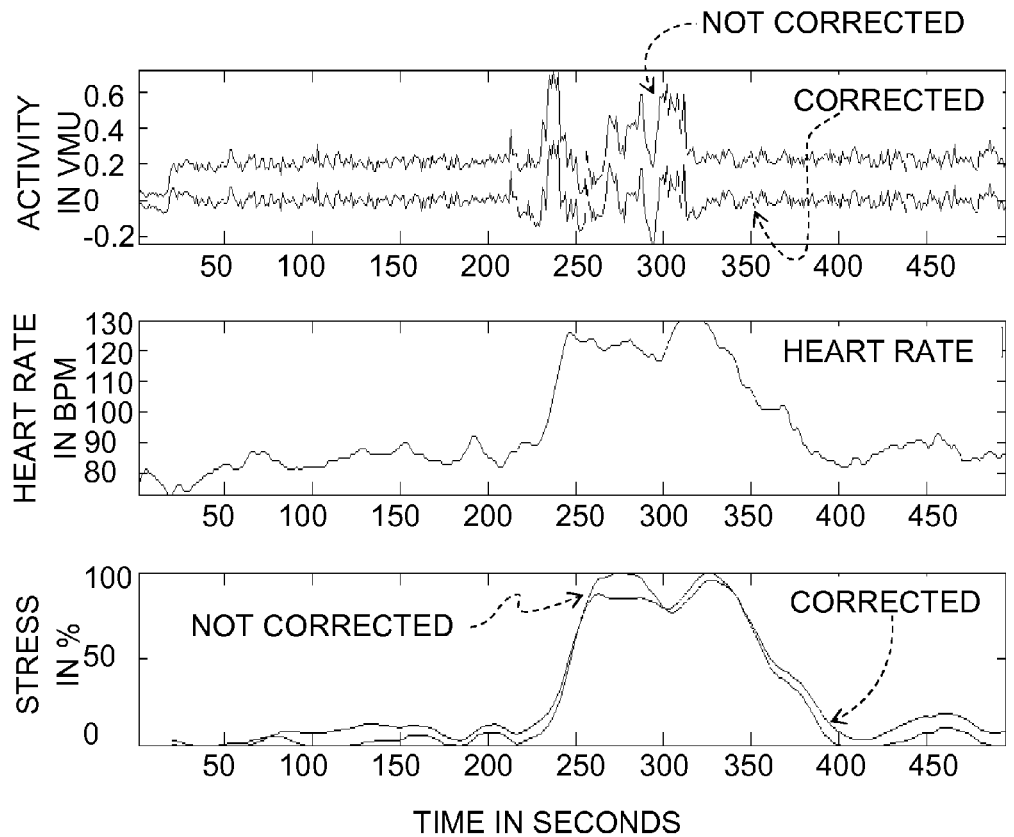

FIG. 4 is graphic representation of measurements of activity signal of a horse driver and heart rate signal of the horse driver ($HR_{Total}$) and the resulting stress level of the horse rider during horse riding in a time interval of 500 seconds (activity in VMU (vector magnitude units), heart rate of the horse rider in bpm (beats per minute); stress level of the horse rider (%); a not corrected activity signal and stress level without taking into account the movement of the moving structure and a corrected activity signal and stress level taking into account the movement of the moving structure are shown).

Figure 5:
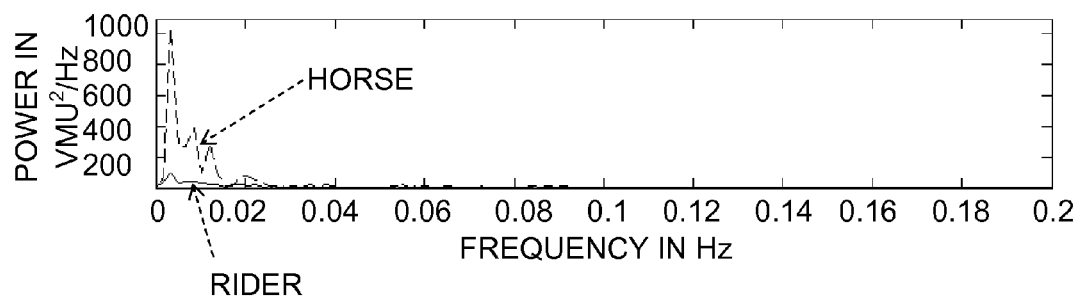

FIG. 5 is a graphic representation of the difference in power spectral density (PSD) between the activity of the horse rider and the horse during the horse riding of FIG. 4.

The invention generally concerns a method and device for obtaining in real-time the mental component of the heart rate, $HR_{Mental}$, as a measure for the stress of an individual.

According to the method, the total heart rate is measured by a heart rate sensor, the movement of the body of the individual is measured by a body sensor and the movement of the moving structure is measured by a moving structure sensor.

The body sensor signal contains information concerning movement of the body of the individual as well as movement of the moving structure. The relative movement can be for example the difference between the body and the moving structure sensor measurements. Alternatively, a deconvolution method between the body sensor measurement and the moving structure sensor measurement can be used to extract the required relative movement. The deconvolution method can be any method that solves the problem of the following equation (2):

$$y(t)=x\_1(t)*x\_2(t)+n(t) \qquad (2)$$

where $x\_1(t)$ and $x\_2(t)$ are the convoluted signals, * denoted convolution, n(t) is a noise signal and y(t) is the measured signal.

Inversely, the activity signal can be extracted by correcting the moving structure sensor measurement for the measurements by the body sensor. Finally, the relative movement can be extracted by performing any of the above methods or by using the body sensor measurement during specific parts of the moving structure sensor measurement (e.g. acceleration, deceleration, lateral movements, etc.) or the body sensor measurement.

Figure 1:
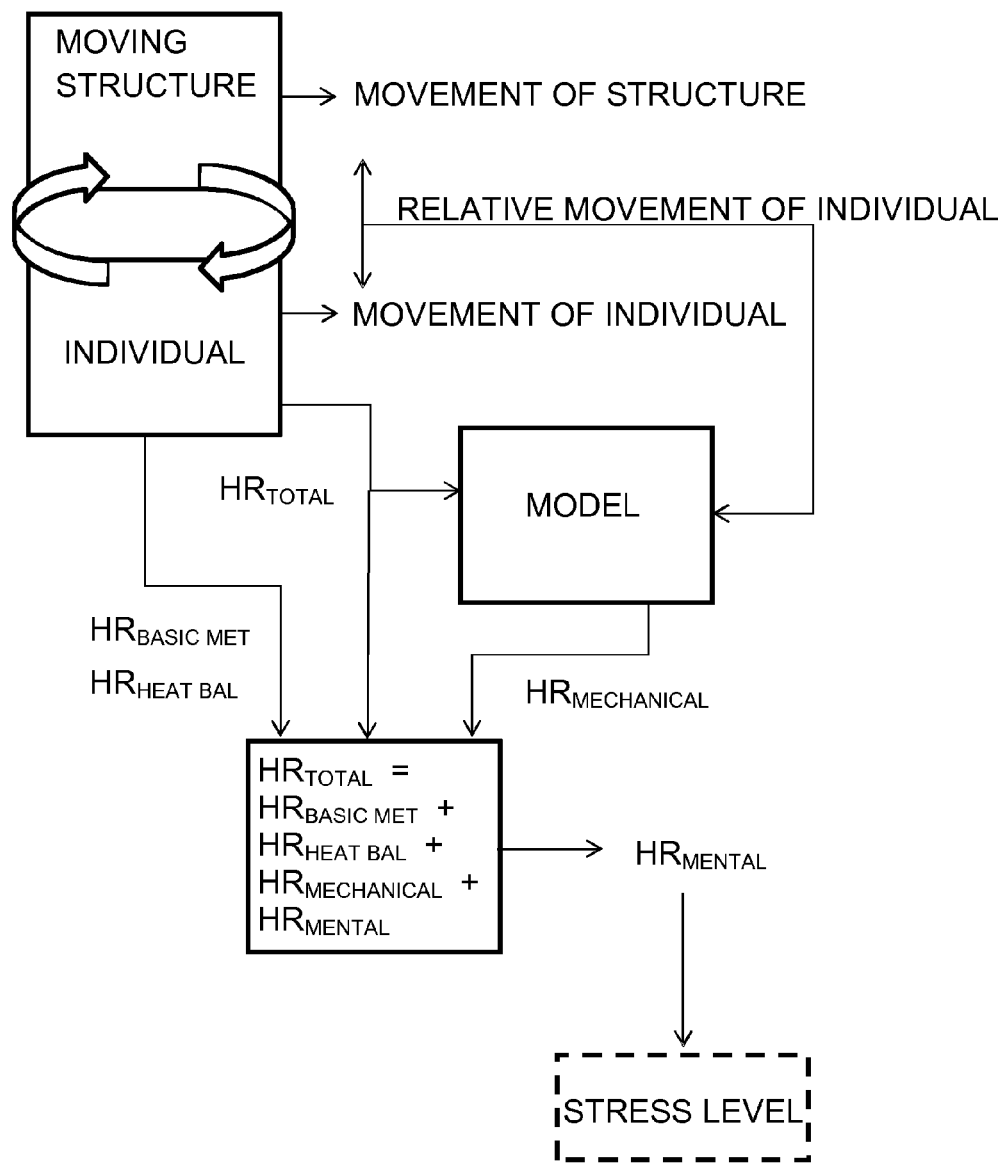
FIG. 1 is a schematic flow chart overview of a preferred embodiment of the method according to the invention.

According to a preferred embodiment of the method the activity component, $HR_{Mechanical}$, is estimated in real-time based on the relative movement of the individual in relation to the moving structure (FIG. 1).

The measured total heart rate signal, $HR_{Total}$, contains information concerning e.g. the mental component, $HR_{Mental}$, and the activity component, $HR_{Mechanical}$.

A real-time estimation of the stress level, corresponding to the mental component, $HR_{Mental}$, in the heart rate signal is obtained from the estimated activity component, $HR_{Mechanical}$, and the measured total heart rate, $HR_{Total}$.

According to the invention, the body activity that requires energy from the heart is measured by measuring how the body is moving within the moving structure or in relation to the movement of the moving structure. The body activity or the body movement that requires metabolic energy is expressed in the way on how the body is moving in relation to the movement of the moving structure. A living organism in or on a moving structure will move in a different way than a non-living object in or on a moving structure. This difference in movement takes energy from the muscles in the body and consequently relates to the resulting heart rate of the individual in that situation.

Hence, a relative movement of the individual in relation to the moving structure is determined based on the real-time movement of the individual and the real-time movement of the moving structure. The relative movement may be calculated and/or estimated based on a model.

One way to get a measure for this body movement that requires metabolic energy is to compare the movement of the body as measured by for example a 3D accelerometer worn on the body with the movement measured by a 3D accelerometer on the moving structure or vehicle. Standing up in a moving subway train for example takes muscle energy and these results in a body movement that is different from the movement of the moving vehicle. Depending on the movement of the moving structure or vehicle (e.g. acceleration or deceleration), the difference in movement will increase or decrease.

A measure for this difference in movement between an active body of the individual and the moving structure or vehicle generates a measure for the metabolic energy that is required to keep the body in position and/or is the so called "mechanical component of heart rate" for a body in a moving structure or vehicle.

It means that by having a measure for the movement, the method as described in international patent application WO2008/003148A1 can be applied to estimate the mental component in the equation (1) by making use of this movement as the activity input signal for estimating the activity component $HR_{Mechanical}$.

A device for monitoring stress of an individual according to the invention comprises preferably at least (a) an input unit for measuring in real-time input values comprising
   a total heart rate ($HR_{Total}$) of the individual,
   a movement of the individual,
   a movement of the moving structure;
(b) a memory unit for storing the input values;
(c) a calculating unit for estimating in real-time
   a mechanical component ($HR_{Mechanical}$) of the heart rate based on the real-time movement of the individual and the real-time movement of the moving structure, using a dynamic and adaptive data-based on-line modelling technique,
   a mental component ($HR_{Mental}$) of the heart rate obtained by subtracting the mechanical component ($HR_{Mechanical}$) of the heart rate, a component of the heart rate relating to heat balance ($HR_{Heat\ Bal}$) and a component of the heart rate relating to basic metabolic functions ($HR_{Basic\ Met}$) from the total heart rate ($HR_{Total}$);
(d) an output unit for displaying an output value comprising a stress level corresponding to the mental component ($HR_{Mental}$) of the heart rate.

Figure 2:
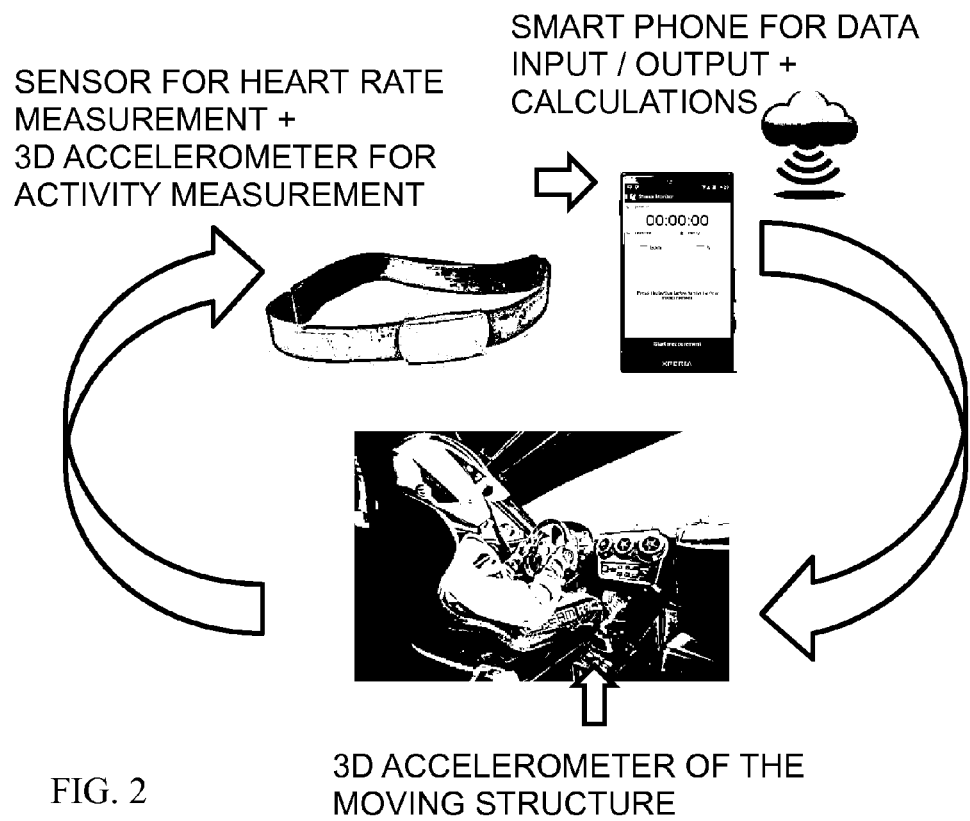
FIG. 2 is a schematic representation of the method and device according to an embodiment of the invention comprising e.g. two accelerometers, a heart rate sensor and a smart phone processing unit.

An embodiment of a method and device according to the invention is schematically shown in FIG. 2.

As shown in FIG. 2 a way to measure the required signals is a heart rate measurement on the individual, a first 3D accelerometer on the body of the individual and a second 3D accelerometer attached in the car.

The input unit may comprise a smart phone connected with a heart rate sensor in a belt and one or more accelerometers. The heart rate sensor attached with the belt to the individual measures the total heart rate ($HR_{Total}$) of the individual. The first 3D accelerometer measures the movement of the body of the individual. The second 3D accelerometer measures the movement of the car.

Alternatively, instead of the second 3D accelerometer, car movement may be estimated from the body movement by using an additional equation or model.

The smart phone may be used for collecting in real-time the input values, i.e. the total heart rate ($HR_{Total}$) of the individual, the movement of the individual and the movement of the moving structure, i.e. the car. The smart phone may further be used as memory unit for storing the input values and as a calculating unit for estimating in real-time the mechanical component ($HR_{Mechanical}$) and the mental component ($HR_{Mental}$). Possibly the smart phone may also transfer the collected data to a remote memory and/or calculating unit.

The smart phone may further be used as the output unit for displaying an output signal, which relates to a stress level corresponding to the mental component ($HR_{Mental}$) of the heart rate. The level of stress may be correlated with the mental component ($HR_{Mental}$) of the heart rate and expressed as a percentage of a maximal value.

Figure 3:
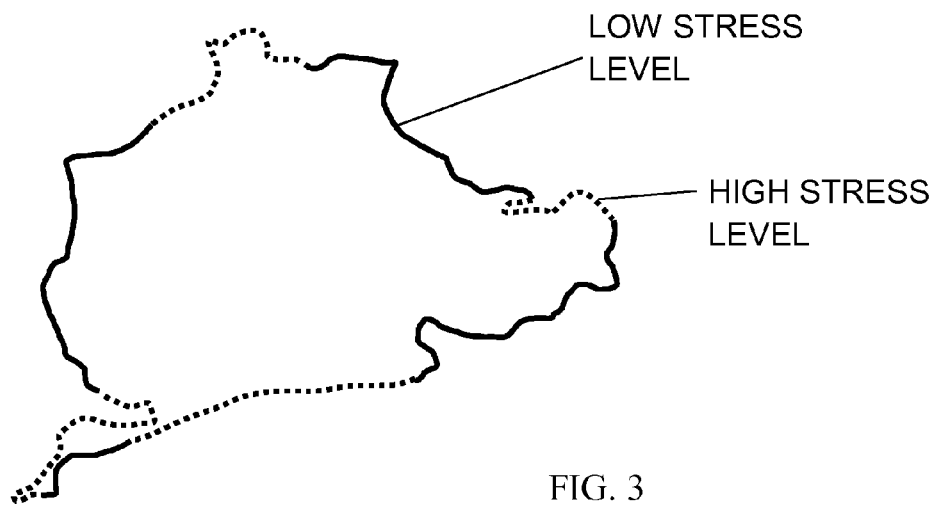
FIG. 3 is a schematic representation of a possible output according to the embodiment of FIG. 2 comprising the course of a race circuit with indication of parts in which higher levels of mental stress of the individual are detected. As such

As shown in FIG. 3 by applying the method of the invention, it now is possible to monitor in real-time the stress levels of for example car drivers in races. This allows measuring the real-time stress of race drivers in relation to their performance, position on the track, events happening during a race etc.

A horse rider on a horse is another example of an individual, i.e. the horse rider, in a moving structure, i.e. the horse.

The measured activity signal and heart rate signal ($HR_{Total}$) of the horse rider during horse riding in a time interval of 500 seconds in which several obstacles are passed is shown in FIG. 4. From the activity signal and heart rate signal the stress level of the horse rider is calculated, also shown in FIG. 4.

The total heart rate of the horse rider is measured in beats per minute (bpm) by a method which is known as such by the skilled in the art.

The activity of both the individual and the moving structure are measured by a 3D accelerometer, in particular a first Zephyr 3D accelerometer is fixed to the horse and a second Zephyr 3D accelerometer is fixed to the horse rider.

The activity in FIG. 4 is displayed in vector magnitude units (VMU). Both a corrected signal taking into account the movement of the moving structure and the not corrected signal are shown. From these signals and the heart rate signal a respective corrected and not-corrected stress level is calculated.

The correction of the activity signal of the horse rider of FIG. 4 taking into account the movement of the moving structure, i.e. the horse, may be done as follows.

In a first step the power spectral density (PSD) is calculated of activity of both the individual, i.e. the human body of the horse rider, and the activity of the moving structure, i.e. the horse. These activities are measured in Vector Magnitude Units (VMU) using the fast Fourier transform. VMU is used since the range of movement is depending on the type of moving structure. The range indeed doesn't matter since what matters is which part of the movement of the human body is due to the movement of the moving structure and needs no metabolic energy and which part of the movement of the body requires metabolic energy produced by the body and consequently needs heart rate activity.

The observation was that for specific moving structures, for example the horse rider on the moving horse, in the lowest frequencies, in this case between 0 Hz and 0.05 Hz, the Power Spectrum Density of the moving structure, i.e. the horse, is dominant. This is illustrated in FIG. 5.

The difference in PSD can be explained by the fact that the activity of the moving structure contains more low frequency information than the individual's, i.e. human's, measured activity. Accordingly, a second order high pass filter, for example a Butterworth high pass filter, can be applied to the human's measured activity as a way of removing the activity component of the moving structure from the measured activity of the individual, i.e. the human body. The cut-off frequency of the filter can be chosen per measurement in an iterative way. Initially it is for example set at 0 Hz before being increased until a frequency is reached for which the power in the measured activity of the moving structure is no longer higher than power in the activity of the individual, i.e. the human body. In the end, an average cut-off frequency can be used for the moving structure with the assumption that every moving structure has a particular activity that is characterised by particular frequency content.

The invention is not restricted to the embodiments of the method and device according to the invention as described above. Thus, besides an accelerometer for measuring the activity of an individual, a global positioning system (GPS) device or a video camera may be used as well.

REFERENCES

Taylor C. J., Pedregal D. J., Young P. C., Tych W. 2007. Environmental time series analysis and forecasting with the Captain toolbox. Environ Modell Softw 22: 797:814.

Young P. C. 2011. Recursive estimation and time-series analysis: an introduction for the student and the practitioner. Springer, Heidelberg.

The invention claimed is:

1. A method for monitoring stress of an individual in a moving structure by estimating and monitoring a mental component of a total heart rate of the individual,
whereby the total heart rate ($HR_{Total}$) comprises a mechanical component ($HR_{Mechanical}$) and the mental component ($HR_{Mental}$), and
the total heart rate ($HR_{Total}$) further comprises a component relating to heat balance ($HR_{Heat\ Bal}$) and a component relating to basic metabolic functions ($HR_{Basic\ Met}$),
wherein the method comprises the steps of
measuring a movement of the individual in real-time,
measuring a movement of the moving structure in real-time,
estimating the mechanical component ($HR_{Mechanical}$) in real-time based on the real-time movement of the individual and the real-time movement of the moving structure,
measuring the total heart rate ($HR_{Total}$) in real-time,
obtaining the mental component ($HR_{Mental}$) by subtracting the mechanical component ($HR_{Mechanical}$), the component relating to the heat balance ($HR_{Heat\ Bal}$) and the component relating to basic metabolic functions ($HR_{Basic\ Met}$) from the total heart rate ($HR_{Total}$), and
outputting a level of stress corresponding to the mental component ($HR_{Mental}$).

2. The method according to claim 1, wherein the estimating of the mechanical component ($HR_{Mechanical}$) is done by using a dynamic and adaptive data-based on-line modelling technique.

3. The method according to claim 1, wherein a relative movement of the individual in relation to the moving structure is determined based on the real-time movement of the individual and the real-time movement of the moving structure.

4. The method according to claim 3, wherein the mechanical component ($HR_{Mechanical}$) is estimated in real-time based on the relative movement of the individual in relation to the moving structure.

5. The method according to claim 3, wherein the relative movement of the individual in relation to the moving structure is determined by a deconvolution method using real-time measurements of movement of the individual and the moving structure.

6. The method according to claim 1, wherein the mechanical component ($HR_{Mechanical}$) is estimated in real-time based on a measured dynamic response of the total heart rate ($HR_{Total}$) to the real-time movement of the individual and the real-time movement of the moving structure.

7. The method according to claim 1, wherein the movement of the individual is measured in real-time by a first accelerometer fixed to the individual.

8. The method according to claim 1, wherein the movement of the moving structure is measured in real-time by a second accelerometer fixed to the moving structure.

9. The method according to claim 1, wherein the component relating to the heat balance ($HR_{Heat\ Bal}$) and a component relating to basic metabolic functions ($HR_{Basic\ Met}$) are considered to be constant for the individual during activity in the moving structure.

10. The method according to claim 1, wherein it comprises the step of correcting the movement of the individual in real-time taking into account the movement of the moving structure.

11. The method according to claim 10, wherein the estimating of the mechanical component ($HR_{Mechanical}$) is based on the corrected real-time movement of the individual.

12. A device for monitoring stress of an individual comprising
(a) an input unit for measuring in real-time input values comprising
a total heart rate ($HR_{Total}$) of the individual,
a movement of the individual,
a movement of the moving structure;
(b) a memory unit for storing the input values;
(c) a calculating unit for estimating in real-time
a mechanical component ($HR_{Mechanical}$) of the heart rate based on the real-time movement of the individual and the real-time movement of the moving structure, using a dynamic and adaptive data-based on-line modelling technique,
a mental component ($HR_{Metal}$) of the heart rate obtained by subtracting the mechanical component ($HR_{Mechanical}$) of the heart rate, a component of the heart rate relating to heat balance ($HR_{Heat\ Bal}$) and a component of the heart rate relating to basic metabolic functions ($HR_{Basic\ Met}$) from the total heart rate ($HR_{Total}$);
(d) an output unit for displaying an output value comprising a stress level corresponding to the mental component ($HR_{Mental}$) of the heart rate.

\* \* \* \* \*